United States Patent [19]

Pierce et al.

[11] 4,340,058
[45] Jul. 20, 1982

[54] SANITARY NAPKIN

[76] Inventors: Larry L. Pierce; June S. Pierce, both of 4120 Vansant Rd., Douglasville, Ga. 30135

[21] Appl. No.: 213,233

[22] Filed: Dec. 5, 1980

[51] Int. Cl.³ .................................. A61F 13/16
[52] U.S. Cl. ........................ 128/287; 128/290 B; 128/DIG. 30
[58] Field of Search ........... 128/270, 285, 287, 284, 128/290 R, 290 P, 290 B, 296, DIG. 30

[56] References Cited

U.S. PATENT DOCUMENTS

| | | | |
|---|---|---|---|
| 1,967,859 | 7/1934 | Burns | 128/290 |
| 2,351,836 | 6/1944 | Popper | 128/285 |
| 3,397,695 | 8/1968 | Voss | 128/270 |
| 3,726,277 | 4/1973 | Hirschman | 128/285 |
| 3,845,767 | 11/1974 | Friese et al. | 128/270 |
| 3,911,921 | 10/1975 | Svensson | 128/DIG. 30 |
| 3,983,873 | 10/1976 | Hirschman | 128/285 |
| 4,055,184 | 10/1977 | Karami | 128/287 |
| 4,196,562 | 4/1980 | Hirschman | 128/270 |

Primary Examiner—Robert W. Michell
Assistant Examiner—C. W. Shedd
Attorney, Agent, or Firm—George M. Thomas

[57] ABSTRACT

A plurality of elongate absorbent pads, each of approximately circular cross-section, are arranged parallel to one another in a pyramid shaped bundle, with a first layer of pads arranged in parallel, side-by-side relationship, the layers of pads above the first layer of pads arranged in side-by-side relationship and overlying the layer of pads next below at positions over the adjacent surfaces of adjacent ones of the pads in the layer next below. The pads are movable with respect to one another, a liquid pervious tubular sock surrounds and encloses the pads, a sheet of liquid impervious material substantially covers the bottom portion of the first layer of pads, and a layer of adhesive material is disposed on the bottom portion of the napkin for securing the napkin to an undergarment.

13 Claims, 13 Drawing Figures

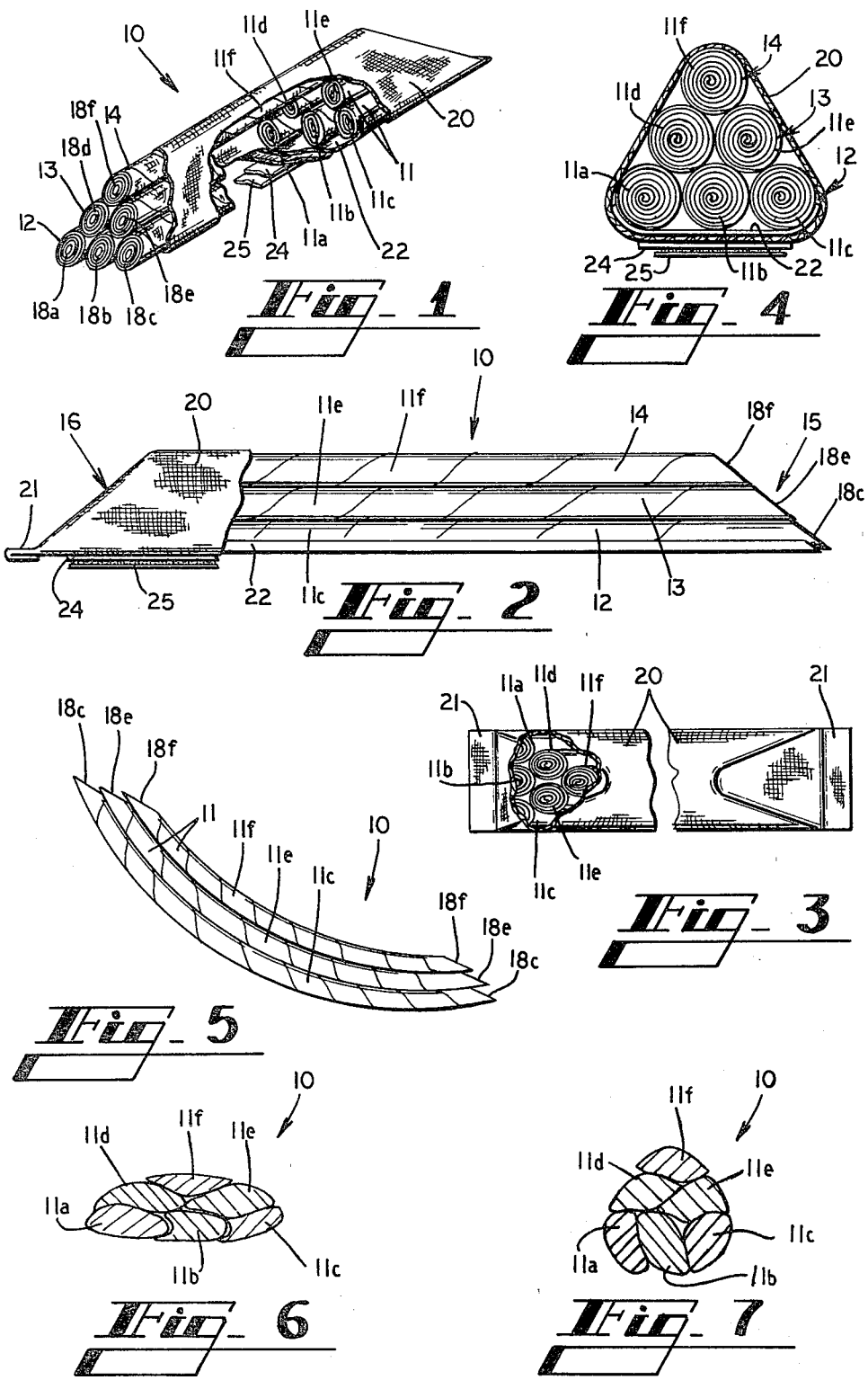

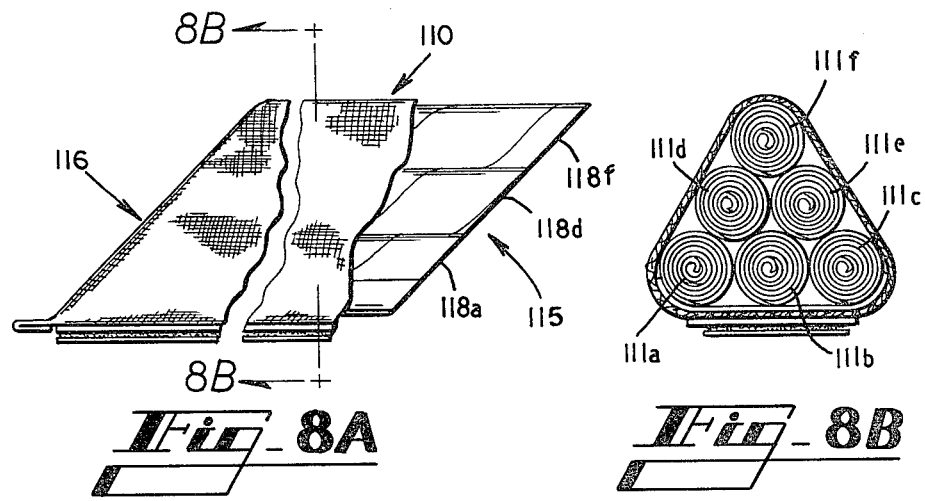
Fig_8A  Fig_8B
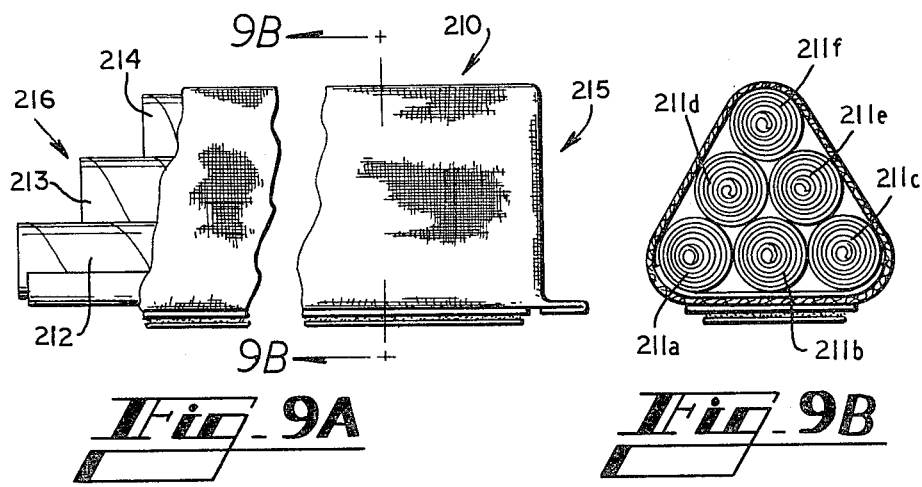
Fig_9A  Fig_9B
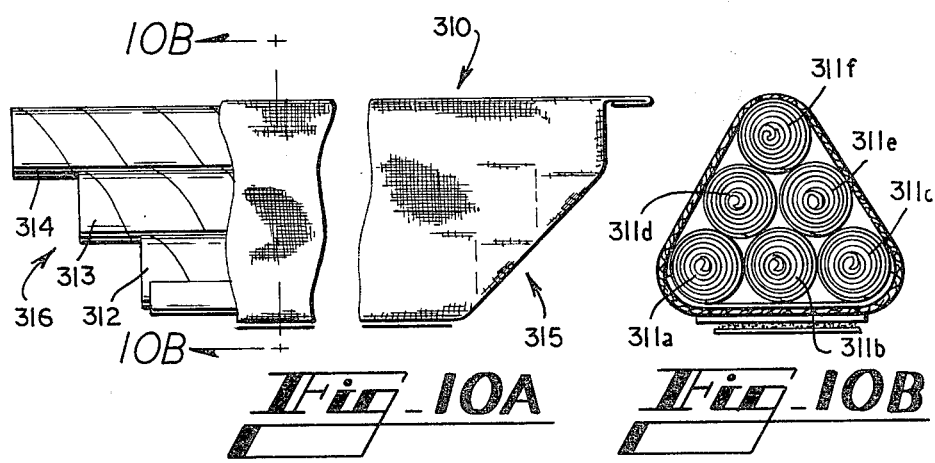
Fig_10A  Fig_10B

SANITARY NAPKIN

BACKGROUND

This invention relates to a sanitary napkin which is formed from liquid absorbent material and is worn for collection of menstrual fluids.

Sanitary napkins or pads which are worn for the collection of menstrual fluids must be of sufficient bulk and absorbency in order to function to collect fluids but the relatively thick napkins usually are uncomfortable to the wearer, and when the thick napkins are compressed during normal use by the wearer, the material of the napkin is less capable of absorbing and retaining the fluids. Additionally, sanitary napkins sometimes tend to become twisted or shifted out of proper position when in use, causing discomfort to the wearer and reducing the effectiveness in the collection of fluids.

Various stiffners, belts and adhesive strips have been used in the past in order to help sanitary napkins to retain their shape and to keep their position during use, but these features have not been completely effective in solving the above-listed problems.

SUMMARY OF THE INVENTION

Briefly described, the present invention comprises a sanitary napkin which is to be worn for the collection of menstrual fluids, and which comprises a plurality of elongated pads arranged parallel to one another in a pyramid-shaped bundle and wrapped with a liquid-permeable wrapper or sock, with a liquid impermeable sheet covering the lower surface of the bottom layer of pads. The pads are movable relative to one another, both longitudinally and laterally, and the napkin can be bent along its length so as to conform to the shape of the anatomy. In some embodiments of the invention the ends of the napkin are wedge-shaped so as to flair or merge with the anatomy of the wearer. In one embodiment the pads are circular in cross-section and comprise absorbent sheet material wound upon itself in a spiral configuration, and the pads are compressible so as to flatten in response to body weight or movement.

Thus, it is an object of this invention to provide a sanitary napkin for use in the collection of menstrual fluids, which is comfortable to the wearer and which is capable of being shaped to the anatomy of the wearer during use.

Another object of this invention is provide a sanitary napkin that comprises a plurality of elongated pads that are movable with respect to one another for the purpose of shaping the napkin during use by the wearer.

Other objects, features and advantages of the present invention will become apparent upon reading the following specification, when taken in conjunction with accompanying drawings.

BRIEF DESCRIPTION OF THE DRAWINGS

FIG. 1 is a perspective illustration of the sanitary napkin, with portions removed for clarity.

FIG. 2 is a side elevational view of the sanitary napkin, with the cover partially removed.

FIG. 3 is a top view of the sanitary napkin, with a portion of the cover removed.

FIG. 4 is an end cross-sectional view of the sanitary napkin.

FIG. 5 is a side elevational view of the pads of the sanitary napkin, with the pads shown in a curved configuration.

FIG. 6 is an end cross-sectional view of an end portion of the sanitary napkin, showing a typical configuration of the pads when they have experienced vertical compression.

FIG. 7 is an end cross-sectional view of a central portion of the sanitary napkin, similar to FIG. 6, but showing a typical configuration of the pads when they have experienced lateral compression.

FIGS. 8A, 9A and 10A are side elevational views of second, third and fourth embodiments of the sanitary napkin, with the covers partially removed from one end and with the middle portions removed to shorten the drawing figures.

FIGS. 8B, 9B and 10B are end cross-sectional views of the second, third and fourth embodiments, taken along lines 8B, 9B and 10B of FIGS. 8A, 9A and 10A, respectively.

DETAILED DESCRIPTION

Referring now in more detail to the drawings, in which like numerals indicate like parts throughout the several views, FIG. 1 illustrates the sanitary napkin 10 which comprises a plurality of elongated pads 11 which are arranged parallel to one another in a pyramid shaped bundle. The first layer 12 of pads comprises pads 11a, 11b and 11c, the second layer 13 comprises pads 11d and 11e, and the third layer 14 comprises pad 11f. Pads 11a, 11b and 11c of the first layer 12 are arranged in side-by-side relationship, and the pads 11d and 11e which are positioned above the first layer of pads are also arranged in side-by-side relationship and overly the layer of pads next below at positions over the adjacent surfaces of adjacent ones of the pads in the layer next below. Similarly, pad 11f in the upper layer overlies pads 11d and 11e at a position over the adjacent surfaces of the pads.

As illustrated in FIG. 2 the end portions 15 and 16 of the napkin are formed at an angle, with the end surfaces 18a-18f of each pad 11a-11f being formed at an angle, and with the end surfaces 18a-18f at each end of the napking being located in a common plane. The angle illustrated in the disclosed embodiment is approximately 45°.

The pads 11 illustrated herein comprise absorbent sheet material formed in a spiral roll which is approximately circular in cross-section. The sheet material can comprise any absorbent material, for example a non-woven, porous and dry formed web weighing from about 0.25 to 1.0 ounces per square yard, with the web consisting of unfinished polyolefin or polyester fibers, preferably with the fibers being characterized by surfaces which are devoid of lubricants, anti-static or wetting agents, with the web being intermittently autogenously bonded at discrete bond areas and disposed in a density of about 50 to 3,200 per square inch to permit the passage fluid of therethrough. Other materials such as hydrophilic foam sheet material formed of hydrophilic polymer can be used. While the elongate pads can be easily formed by rolling a non-woven fabric about an axis to thereby form a rolled body portion, it would be understood that the pads can be tubular in that a central opening can extend through the pads, or that the pads can be formed from non-woven material that is not in sheet form.

As illustrated in FIGS. 1-4, a liquid pervious sheet or wrapper 20 surrounds the bundle of pads 11 and holds the pads in their stacked, pyramid shape. Wrapper 20 is tubular and preferably is formed of resilient material so that it has a tensile resilience with respect to pads 11 and tends to hold the pads in their stacked relationship with respect to one another. The wrapper 20 is gathered at the tapered end portions 15 and 16 of the napkin, and in the illustrated embodiment the ends of the wrapper are closed by thermoplastic strips 21 which are folded about the ends of the wrapper and are heat sealed to the ends of the wrapper.

A sheet 22 of liquid impervious material spans the bottom surface of the first layer of pads, so as to substantially cover the bottom portion of the bundle of pads inside the tubular wrapper 20. The sheet 22 is of a length approximately equal to the length of the lower pads 11a-11c and is of a width that extends about a portion of the outside surfaces of the pads 11a and 11c at the sides of the bottom layer of pads. Thus, sheet 22 is turned upwardly at its side edges.

The napkin 10 can be used with a belt or a layer of adhesive material can be applied to the bottom surface of the napkin for securing the napkin to an undergarment. For example, a strip of material 24 having adhesive applied to both surfaces extends along the bottom surface of the napkin, with one adhesive surface facing the bottom surface of the napkin and adhering thereto. The other adhesive face of the strip 24 is covered with a removable strip 25 until the napkin is to be used. The strip 25 is simply peeled away from the strip 24 to expose the adhesive.

As illustrated in FIG. 5, the napkin 10 can be curved along its length, with the pads 11 being movable longitudinally with respect to one another. For example, the pad 11f of the upper or third layer can shift longitudinally with respect to the pads 11d and 11e, and pads 11d and 11e can shift longitudinally with respect to pads 11a, 11b and 11c. The shifting of the pads 11a-11f with respect to one another permits the napkin to be more flexible or bendable so as to conform to the shape of the anatomy of the wearer.

As illustrated in FIGS. 6 and 7, the elongated pads 11 can be shifted or moved laterally with respect to one another. For example, when vertical forces are applied to the napkin, as when the wearer of the napkin sits on an end portion of the napkin, the pads 11d and 11e of the second layer 13 tend to work down in between the pads 11a, 11b and 11c, and each pad tends to flatten against its adjacent compressing surfaces. In addition, the pads 11a, 11b and 11c tend to flatten out and to spread apart slightly and the pads 11d and 11e also tend to flatten out and to move into any gaps formed between pads 11a, 11b and 11c and they move apart slightly so as to permit the pad 11f of the third layer 14 to move downwardly between the pads 11d and 11e of the second layer. The overall result is that the pads 11 spread laterally and the upper pads tend to move into the spaces formed between the lower pads, and all the pads tend to be compressed slightly with the overall napkin assuming a lower profile.

When lateral forces are applied to the opposite sides of the napkin 10, as when the legs of the wearer of the napkin press laterally against the sides of the central portion of the napkin, the pads 11 tend to shift vertically with respect to one another. As illustrated in FIG. 7, the pads 11a, 11b and 11c tend to be formed in an elliptical cross-sectional shape as they are compressed laterally, causing them to occupy more vertical space. The pads 11d and 11e of the second layer of pads still tend to stay in their relative positions with respect to one another and with respect to the pads next below, but they also tend to assume a tall cross-sectional shape. Similarly, the pad 11f in the upper layer still occupies the groove formed by the pads 11d and 11e in the layer next below, but also tends to assume a more vertical profile. In some conditions, the outside pads 11a and 11c of the first layer may tend to work between pad 11b of the first layer and pads 11d and 11e of the second layer. In general, the lateral compression of the napkin results in the pads shifting and reshaping themselves so as to cause the napkin to assume a more vertical profile and to occupy less lateral space.

When the napkin is in use, it is likely that the central portion of the napkin between its sloped ends will be compressed laterally so that the elongated pads 11 in the central portion of the napkin tend to assume a narrow, tall configuration somewhat similar to that shown in FIG. 7, due to lateral forces applied to the napkins by the legs of the wearer, while one or both end portions of the napkin are likely to assume a wide, short profile somewhat similar to that illustrated in FIG. 6, due to vertical forces applied to the napkin from body movement, sitting, or other activities. Inasmuch as the elongated pads 11 tend to fit into the recesses formed by adjacent ones of the pads, the pads tend to remain in their respective positions even though the pads may become compressed themselves or be pushed laterally into the spaces formed between adjacent ones of the pads, so that no twisting of the overall napkin is likely to occur.

As illustrated in FIGS. 8a and 8b, wherein a second embodiment of the invention is disclosed, the end portions 115 and 116 of the napkin are formed in substantially parallel configurations, with the end surfaces 118a-118f of each pad 111a-111f being formed at an angle, and with the end surfaces 118a-118f at each end of the napkin being located in a common plane As illustrated in FIGS. 9a and 9b, a third embodiment of the invention is disclosed, wherein the end portion 215 of the napkin is flat and formed at a right angle with respect to the length of the pads 211a-211f, while the other ends of each pad 211a-211f are also flat and formed at a right angle with respect to the length of the pads, but the pads are of different lengths. The first layer 212 of pads is longer than the second layer 213, and the second layer is longer than the third layer 214.

The staggered relationship of the pads 211a-211f can be present at both ends of the napkin 210, if desired.

As illustrated in FIGS. 10a and 10b, a fourth embodiment of the invention is illustrated, wherein the pads 311a-311f are formed of different lengths with the first layer 312 of pads being shorter than the second layer 313, and with the second layer being shorter than the third layer 314. Again, the end surfaces of the pads 311a-311f are formed at right angles with respect to the lengths of the pads.

In all of the embodiments of the sanitary napkin as described herein, the pads are formed in a pyramid-shape bundle and wrapped with a liquid pervious wrapper. The configuration of the ends of the napkin can be modified by shaping the ends of the pads and by adjusting the lengths of the pads with respect to one another in the bundle.

While the napkin has been disclosed as a sanitary napkin for use in the collection of menstrual fluids, it should be understood by those skilled in the art that the napkin can be used for other purposes. For example, the napkin can be used as a bandage for the purpose of absorbing blood, sweat or other body fluids on various parts of the anatomy. Additionally, the ends of the tubular sock 20 can be extended so as to form straps that can be tied, pinned or otherwise connected to other garments or to the anatomy.

While this invention has been described in detail with particular reference to a preferred embodiment thereof, it will be understood that variations and modifications can be effected within the spirit and scope of the invention as described hereinbefore and as defined in the appended claims.

We claim:

1. A sanitary napkin comprising a plurality of elongate absorbent pads arranged parallel to one another and in a bundle generally triangular in cross-section with a first layer of pads arranged in side-by-side relationship, a second layer of pads arranged in side-by-side relationship and each pad of the second layer of pads overlying the pads of the first layer of pads at positions over the adjacent surfaces of the adjacent ones of the pads in the first layer, and a third layer of pads comprising at least one pad overlying the pads in the second layer, a liquid pervious material surrounding all of said pads for holding the pads in an uncompressed bundled relationship with the pads movable longitudinally with respect to one another, a sheet of liquid impervious material substantially covering the bottom portion of the first layer of pads, and a layer of adhesive material disposed on the bottom portion of said napkin for securing said napkin to an undergarment, as a result of the napkin not being compressed said napkin being characterized by being bendable along its length with portions of some of the pads movable longitudinally with respect to others of the pads as the napkin is bent along its length whereby the napkin is placed in external contact with the female human body with the third layer of pads in aligned contact with the labia and with the other pads holding the third layer of pads in contact with the labia and bending the napkin along its length as necessary to conform to the curvature of the external surfaces of the anatomy adjacent to the labia.

2. The sanitary napkin of claim 1 and wherein each of said absorbent pads are approximately of circular shape across their lengths.

3. The sanitary napkin of claim 2 and wherein the first layer of pads comprises three pads, the second layer of pads comprises two pads and the third layer of pads comprises one pad, and the ends of the pads at each end of the napkin are formed approximately in a common plane which is sloped from the first layer of the pads at an acute angle inwardly of the napkin.

4. The sanitary napkin of claim 1 and wherein the pads of the first layer of pads are of a length different from the lengths of the pads of the other layers of pads.

5. The sanitary napkin of claim 1 and wherein the ends of some of the pads at one end of the napkin are staggered with respect to each other.

6. The sanitary napkin of claim 1 and wherein said liquid pervious material surrounding said pads comprises a length of tubular material with the pads positioned in and extending longitudinally along the length of tubular material.

7. The sanitary napkin of claim 1 and wherein said sheet of liquid impervious material is positioned between said first layer of pads and said liquid pervious material surrounding said pads.

8. The sanitary napkin of claim 1 and wherein said elongate absorbent pads each comprise a length of sheet material formed in a spiral roll, with each pad being substantially circular in cross-section.

9. A sanitary napkin comprising a plurality of elongate absorbent pads arranged parallel to one another in an elongated uncompressed bundle of approximately triangular cross-section, and a tubular wrapper of a liquid pervious material surrounding all of said pads and closed at its ends about said pads for maintaining the pads in a bundle, and as a result of the napkin not being compressed, portions of said pads are movable with respect to one another along the lengths of the pads and the napkin is bendable along its length when placed in external contact with the female human body with one of the pads aligned with and placed adjacent the labia and with the other pads holding the one pad adjacent the labia and with the napkin curved along its length as necessary to conform to the curvature of the external surfaces of the anatomy.

10. The sanitary napkin of claim 9 and wherein said elongate pads of said bundle are arranged in a pyramid with the first layer of pads arranged in side-by-side relationship, the layers of pads above the first layer of pads arranged in side-by-side relationship and overlying the layer of pads next below at positions over the adjacent surfaces of adjacent ones of the pads in the layer next below.

11. The sanitary napkin of claim 9 and further including a sheet of liquid impervious material substantially covering the bottom portion of the bundle of pads inside said tubular wrapper, and adhesive material disposed on the bottom portion of said napkin for securing said napkin to an undergarment.

12. The sanitary napkin of claim 11 and wherein the side portions of said sheet of impervious material are wrapped about a portion of the pads in the bottom portion of the bundle of pads.

13. The sanitary napkin of claim 9 and wherein the ends of the pads at one end of the napkin are staggered with respect to each other.

* * * * *